United States Patent
Phinney et al.

(10) Patent No.: US 6,913,259 B2
(45) Date of Patent: Jul. 5, 2005

(54) APPARATUS FOR DETECTION OF MULTIPLE DOCUMENTS IN A DOCUMENT TRANSPORT

(76) Inventors: Daniel P. Phinney, 343 State St., Rochester, NY (US) 14650; Jennifer J. Phinney, 343 State St., Rochester, NY (US) 14650; Nelson A. Blish, 343 State St., Rochester, NY (US) 14650; David M. Schaertel, 343 State St., Rochester, NY (US) 14650

(*) Notice: Subject to any disclaimer, the term of this patent is extended or adjusted under 35 U.S.C. 154(b) by 60 days.

(21) Appl. No.: 10/351,698

(22) Filed: Jan. 27, 2003

(65) Prior Publication Data

US 2004/0145110 A1 Jul. 29, 2004

(51) Int. Cl.[7] .............................................. B65H 7/02
(52) U.S. Cl. ............. 271/259; 271/265.02; 271/265.03; 271/265.04; 271/261; 271/262; 340/674
(58) Field of Search ................................. 271/261, 262, 271/263, 259, 258.01, 265.01, 265.02, 265.03; 340/674

(56) References Cited

U.S. PATENT DOCUMENTS

| | | | | |
|---|---|---|---|---|
| 3,932,755 A | * | 1/1976 | Sagawa ....................... 250/349 |
| 4,286,149 A | * | 8/1981 | Ben-Nathan et al. ... 250/223 R |
| 4,807,263 A | * | 2/1989 | Ohno et al. ..................... 377/8 |
| 4,983,854 A | * | 1/1991 | Mizuno et al. ......... 250/559.15 |
| 5,005,192 A | * | 4/1991 | Duss .............................. 377/8 |
| 5,174,562 A | * | 12/1992 | Mizunaga et al. .......... 271/261 |
| 6,212,130 B1 | * | 4/2001 | Brazeal et al. ................ 367/93 |
| 2001/0035603 A1 | | 11/2001 | Graves et al. |

FOREIGN PATENT DOCUMENTS

EP 1 148 012 A2 10/2001
JP 58-078935 5/1983

* cited by examiner

*Primary Examiner*—Patrick Mackey
(74) *Attorney, Agent, or Firm*—Nelson Adrian Blish; Buskop Law Group, P.C.

(57) ABSTRACT

An apparatus for detection of multiple documents (10) in a document transport system comprises a transmitter (15), located on a first side of a document feed path (40), and emits a signal through the document feed path. A reflector (52), located on a second side of said document feed path, reflects the signal through the document feed path. A first sensor detects the signal from the transmitter. A second sensor detects the signal from the transmitter.

31 Claims, 4 Drawing Sheets

APPARATUS FOR DETECTION OF MULTIPLE DOCUMENTS IN A DOCUMENT TRANSPORT

CROSS REFERENCE TO RELATED APPLICATIONS

Reference is made to commonly-assigned copending U.S. patent application Ser. No. 10/303,263, filed Nov. 25, 2002, entitled A METHOD AND APPARATUS FOR DETECTION OF MULTIPLE DOCUMENTS IN A DOCUMENT SCANNER USING MULTIPLE ULTRASONIC SENSORS, by Phinney et al., the disclosure of which is incorporated herein.

FIELD OF THE INVENTION

This invention relates in general to using multiple detectors for sensing multiple document feeds or small documents overlapped with larger documents.

BACKGROUND OF THE INVENTION

Scanners and copiers use document feeders to transport documents into the machine. Mechanisms used for the transportation of documents, including paper or sheets of other material, have the capacity to accidentally pick up more than one document fed from a stack of documents. It is necessary to determine when more than one document is pulled into a document transport since multiple documents may jam the transport or prevent processing some documents. In many cases, the documents fed into the scanner are different sizes. Some smaller documents may be located on one side of a document feed path and not pass under a single position sensor.

There are two general methods for multiple document detection, contact and non-contact. The contact methods include measurement of small thickness changes with a contact foot or sensing arm that is in contact with the documents as they pass through the document transport. The contact foot is connected to a linear voltage differential transducer (LVDT), or a magnet, which is sensed by a Hall Effect Sensor. These sensors can detect changes in thickness of less than 1 $\mu$m ($10^{-6}$ m).

The major disadvantage to the contact method is that anything in contact with moving paper, especially thin paper or ripped paper, can cause a malfunction such as a paper jam. The contact method also requires calibration using the maximum thickness document that will be fed through the document transport. When a thickness is measured which is above the calibration value plus a threshold, typically 30%, it is determined to be a multiple document feed. This method, however, will only work when documents having a uniform thickness are processed. Using a wheel on the end of the contact foot can reduce the chances of paper jam, however, the variations in the diameter of this wheel, due to the nonconformity in manufacturing, must be taken into account during the measurements.

The primary non-contact method for multiple document detection sends ultrasound signals through the document stream to determine if more than one document is present. Sending ultrasound through paper results in attenuation of the ultrasound signal. It is possible to determine the presence of multiple documents by change in attenuation of the signal received. It is also possible to detect multiple documents in a document feed path by changes in the phase of the signal transmitted through the documents. This method is independent of the thickness of the individual documents and is made without making contact with these documents.

There are currently ultrasonic detection system available, which use high frequency sensors to sense multiple zones within a local area. This approach works because the sensors are directional, and the signal from one sensor does not interfere with the signal from other sensors. However, these sensors are also more expensive. Low cost sensors have a wide angle of energy emitted, and if used, the sensors can interfere with each other (cross-talk). The interference often causes the design to fail. The problem cannot be solved by multiplexing individual pulses to the emitters, because not enough energy will be sensed by the detector and the time phasing of the signal is not stable.

U.S. Pat. No. 6,212,130 uses a tilted ultrasonic sensor. This could be used in multiple locations but the cost would be significant, using the more expensive directional high frequency sensors. Other approaches using various combinations of transmitters and sensors add to the cost of the document transport system since both transmitters and sensor are expensive. It is desirable to provide a low-cost yet accurate multiple document detection system using as few components as possible and inexpensive components.

SUMMARY OF THE INVENTION

Briefly, according to one aspect of the present invention, an apparatus for detection of multiple documents in a document transport system comprises a transmitter, located on a first side of a document feed path, which emits a signal through the document feed path. A reflector, located on a second side of the document feed path, reflects the signal back through the document feed path. A first sensor detects the reflected signal from the transmitter. A second sensor, detects the reflected signal from the transmitter. The first and second sensors are located on the same side of the document feed path as the transmitter.

In one embodiment of the present invention the transmitter also comprises a detector which detects the reflected signal and provides an additional point of detection of multiple documents. In another embodiment of the present invention a transmitter transmits a signal at a wide angle through the document feed path which is detected by multiple sensors at various positions along a width of the document feed path. A reflector, located on a side of the feed path opposite the transmitter, runs substantially the entire length the document feed path.

The invention and its objects and advantages will become more apparent in the detailed description of the preferred embodiment presented below.

DETAILED DESCRIPTION OF THE INVENTION

The present invention will be directed in particular to elements forming part of, or in cooperation more directly with the apparatus in accordance with the present invention. It is to be understood that elements not specifically shown or described may take various forms well known to those skilled in the art.

Figure 1:
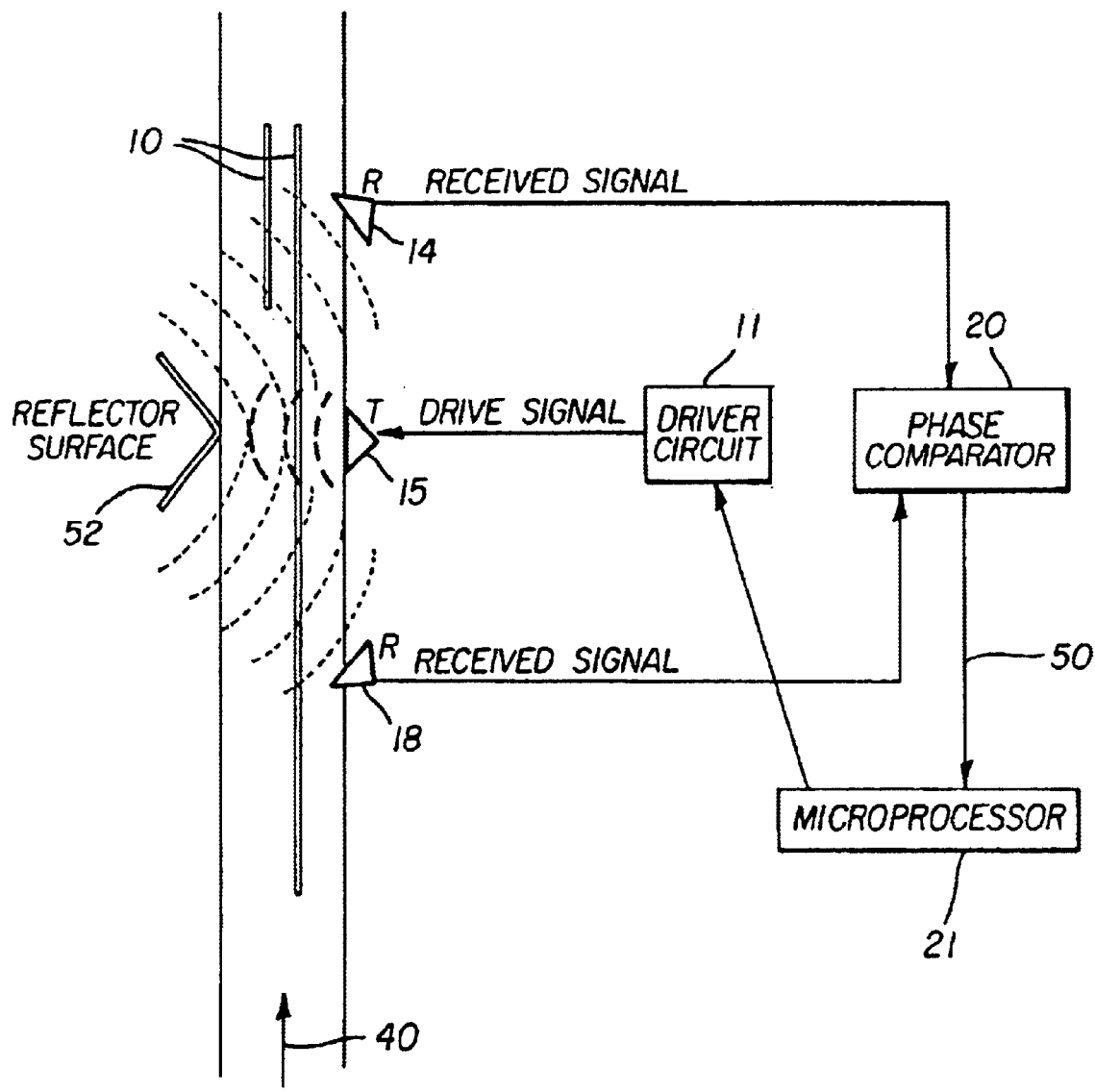
FIG. 1 is a schematic diagram showing paper passing through the system with a double passing through zone A.

Referring now to FIG. 1, an apparatus for multiple document detection 10 in accordance with one embodiment of the present invention is shown. In this particular embodiment, the apparatus includes an ultrasonic drive circuit 11, which provides a drive signal to transmitter 15, as determined by the microprocessor 21. The ultrasonic transmitter produces an ultrasonic signal 30 that passes through a document feed area 40. One or more documents 42 may be transported through document feed area 40. The transmitted ultrasonic signal 30 is reflected by reflector 52. The reflected ultrasonic signal again passes through document feed path 40, and any documents 42 which are in the feed path. The reflected signal is received by ultrasonic receivers 16, 18.

A phase shift of the reflected ultrasonic signal is relatively independent of the thickness of the document or documents in the document feed. This results in a received ultrasonic signal with a phase shift approximately dependent on only the number of documents in the document feed, because of the interfaces between different materials through which the ultrasound passes causes the phase shift, not the total thickness of the documents. While detection of a phase change in the reflected ultrasonic signal is the preferred method of multiple document detection, amplitude detection changes may also be used to detect multiple documents. A combination of amplitude detection and phase change may also be incorporated to add reliability to the multiple document detection system.

The ultrasonic receivers 14, 18 convert the reflected ultrasonic signal into an electrical signal. The electronic signal is sent to a phase comparator 20 wherein the phase difference between the drive signal and the electronic signal is determined. An information signal 50 which represents the determined phase difference is fed from phase comparator 20 to a microprocessor 21.

The microprocessor 21 checks the appropriate information signal to determine if multiple documents are present based on the resulting phase shift or difference between the drive signal and the electronic signal. The microprocessor 21 may also be programmed to detect an amplitude change in the received signal. The change in amplitude of the received signal may also be used to determine the presence of multiple documents. The microprocessor may also be programmed to determine if there are multiple documents present based either on the amplitude signal, the phase change, or a combination of one or both of the signals.

The microprocessor 21 checks for double document feed between receivers 14, 18. The presence of a multiple document detected at receiver 14 or receiver 18 indicates multiple documents in feed path 40. The presence of multiple documents may be used to shut down the document feed transport or sound an alarm to summon an operator.

Although a microprocessor 21 is shown, other types of processors or programmable devices can also be used. Additionally, although in this particular example, an ultrasonic signal is used in this apparatus, other types of signals can also be used.

Figure 2:
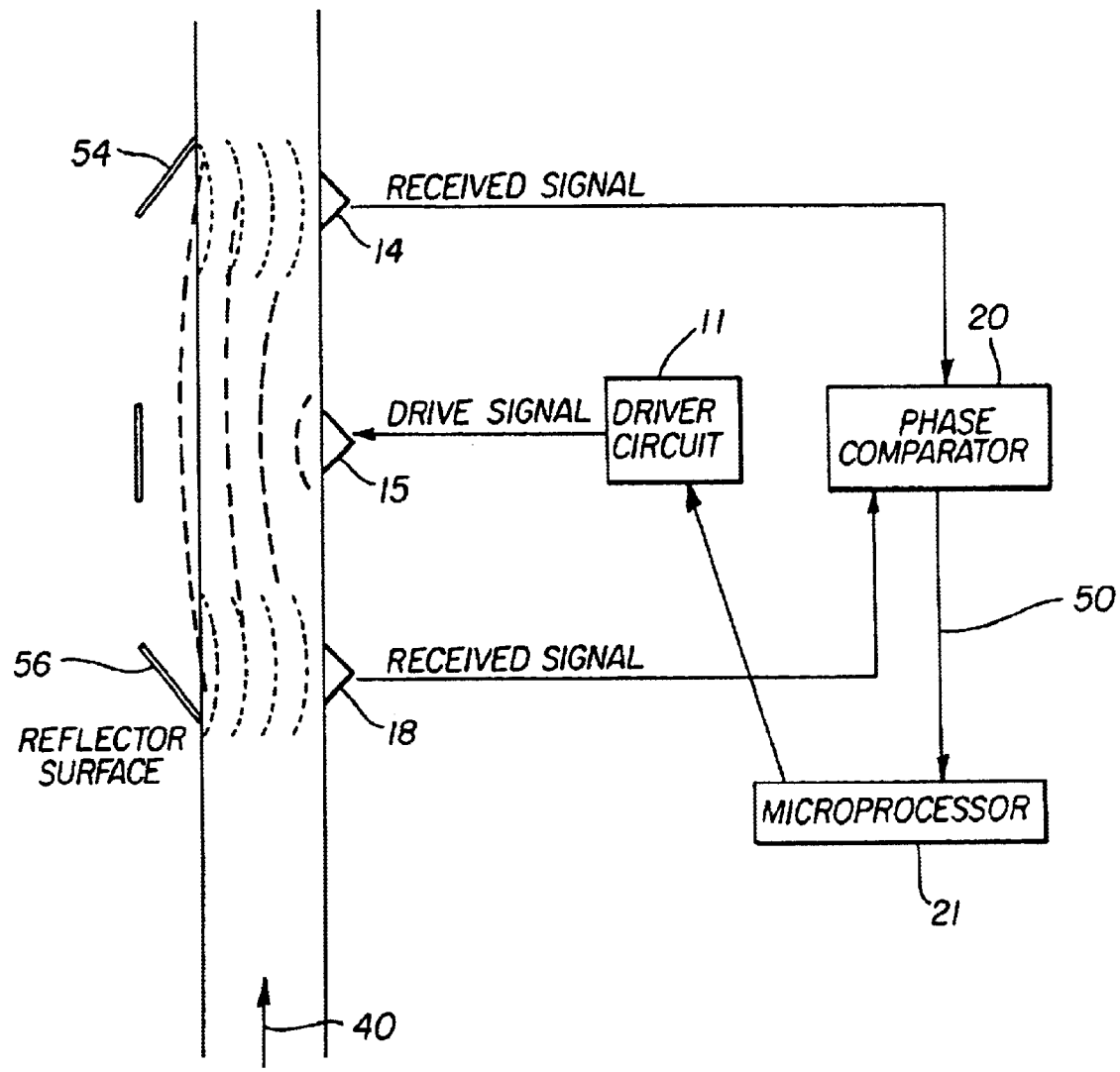
FIG. 2 s a schematic view showing multiple reflectors.

Referring now to FIG. 2, an alternate embodiment of the invention is shown wherein multiple reflectors 54, 55, and 56 are located on a side of the document feed path 40 opposite transmitter 15. Transmitter 15 transmits a wide angle signal which is reflected off reflectors 54, 55, 56. The reflectors are placed at a location and at an angle such that the signal 30 is reflected to an appropriate receiver 14, 18. In this embodiment, as for other embodiments of this invention, transmitter 15 may also receive reflected signals. Used in this fashion the transmitter/receiver 15 provides an additional location in the document feed path 40 for detection of multiple documents.

Figure 3:
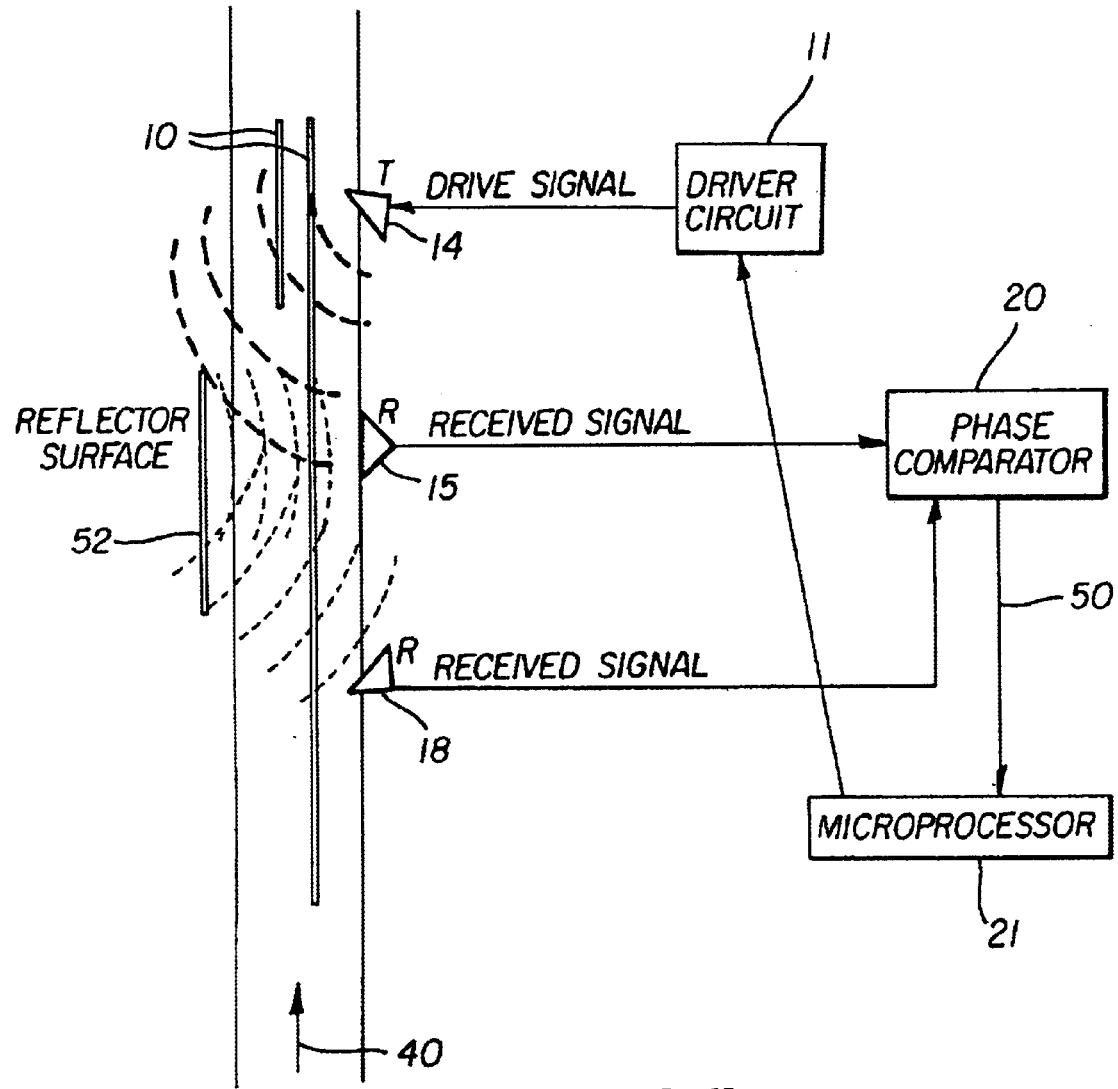
FIG. 3 is a schematic view showing a transmitter located at one edge of a document feed path.

FIG. 3 shows an alternate embodiment of the invention wherein transmitter 15 is located at one edge of document feed path 40. In this embodiment, receivers 14, 18 and transmitter 15 are all equally spaced across document feed path 40. The reflectors are spaced and angled in an appropriate fashion to provide optimal reflection path from the transmitter to the receivers.

Figure 4:
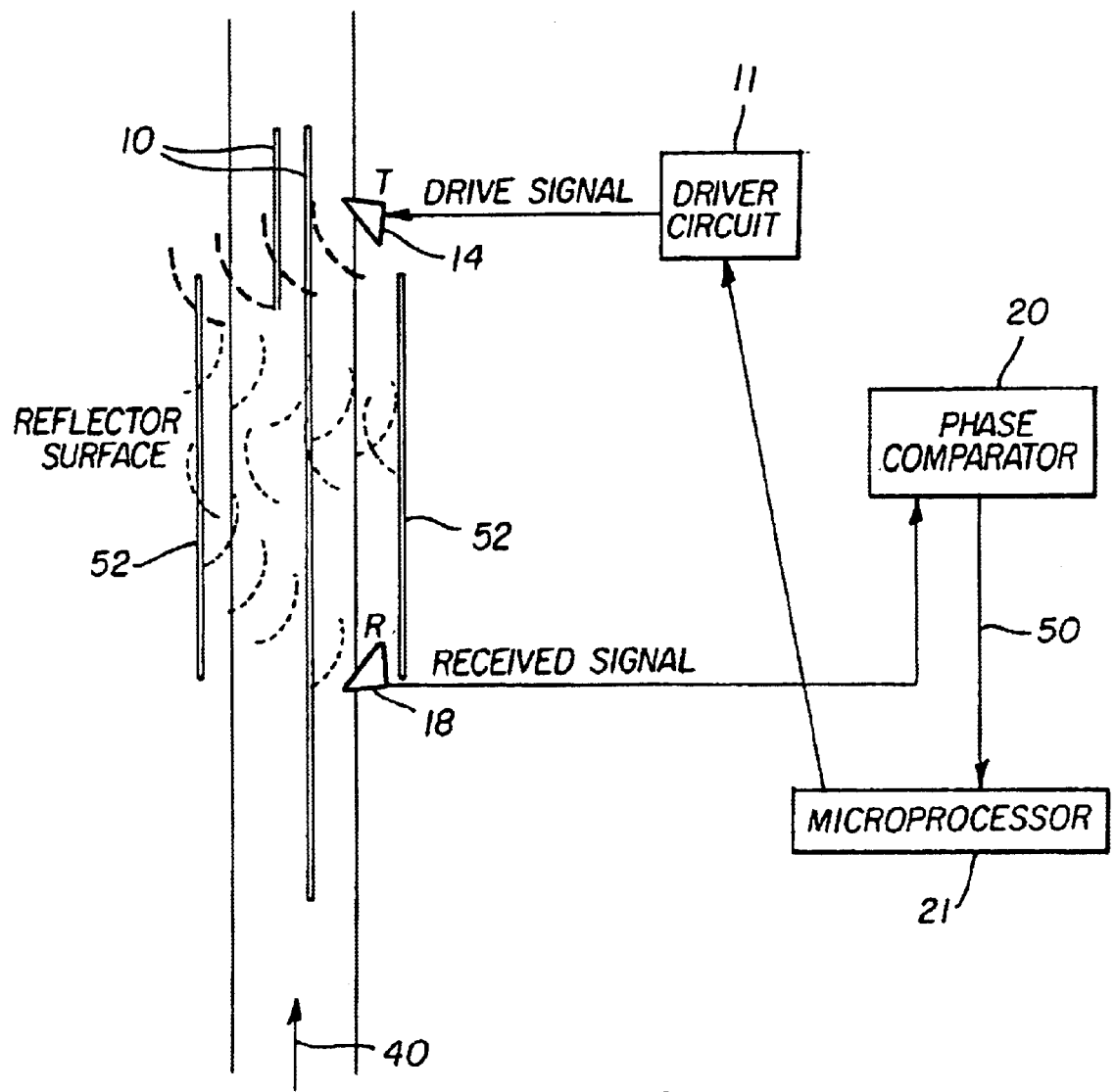
FIG. 4 is a schematic diagram showing a wide angle transmitter with the wall opposite the transmitter comprising a reflective surface.

FIG. 4 is yet another embodiment of the present invention in which the side of the document feed path 40 opposite transmitter 15 is comprised of a reflective material. Transmitter 15 provides a wide angle signal which is reflected off reflector 57 through multiple paths to the receivers. This embodiment eliminates the requirement for separate reflectors, which may further reduce the cost and complexity of the document transport system.

The invention has been described in detail with particular reference to certain preferred embodiments thereof, but it will be understood that variations and modifications can be effected within the scope of the invention.

Parts List

10. Multiple document detection
11. Ultrasonic drive circuit
14. Receiver
15. Transmitter/Receiver
18. Receiver
20. Phase comparator
21. Microprocessor
30. Ultrasonic signal
40. Document feed path
42. Documents
50. Information signal
52. Reflector
54. Reflector
55. Reflector
56. Reflector

What is claimed is:

1. An apparatus for detection of multiple documents in a document transport system consisting of:
   a transmitter, located on a first side of a document feed path, which emits a signal through said document feed path;
   a reflector, located on a second side of said document feed path, which reflects said signal through said document feed path;
   a first sensor for detecting said reflected signal from said transmitter;
   a second sensor for detecting said reflected signal from said transmitter; and
   a microprocessor connected to the transmitter, the first sensor and the second sensor.

2. An apparatus as in claim wherein said signal is an ultrasonic signal.

3. An apparatus as in claim 1 wherein said first sensor and said second sensor are separated by at least one-half a width of said feed path.

4. An apparatus as in claim 1 wherein said transmitter and said reflector are located at a center position with respect to a width of said document transport system.

5. An apparatus as in claim 1 wherein said first sensor is located adjacent said transmitter on said first side of said transmitter.

6. An apparatus as in claim 5 wherein said second sensor is located adjacent said transmitter on said side of said transmitter.

7. An apparatus as in claim 1 wherein said first sensor, said second sensor, and said transmitter are equally spaced across said feed path.

8. An apparatus as in claim 1 wherein said transmitter transmits said signal and receives said reflected signal.

9. An apparatus as in claim 1 wherein a phase change of said signal detected at said first sensor is analyzed to detect multiple documents.

10. An apparatus as in claim 1 wherein an amplitude change of said signal detected at said first sensor is analyzed to detect multiple documents.

11. An apparatus as in claim 1 wherein a phase change of said signal detected at said first sensor or an amplitude change of said signal detected at said first sensor is analyzed to detect multiple documents.

12. An apparatus as in claim 1 wherein a phase change or an amplitude change of said signal detected at either of said first sensor or said second sensor indicates a presence of multiple documents.

13. An apparatus for detection of multiple documents in a document transport system consisting of:
   a transmitter, located on a first side of a document feed path, which emits a signal through a document feed path;
   a first reflector, located on a second side of a document feed path, for reflecting said signal through said document feed path;
   a first sensor, located on a first side of a document feed path, for detecting said reflected signal from said first reflector;
   a second reflector, located on a second side of a document feed path, for reflecting said signal through said document feed path;
   a second sensor, located on a first side of a document feed path, for detecting said reflected signal from said second reflector; and
   a microprocessor connected to the transmitter, the first sensor and the second sensor.

14. An apparatus as in claim 13 wherein said signal is an ultrasonic signal.

15. An apparatus as in claim 13 wherein said first sensor and said second sensor are separated by at least one-half a width of said feed path.

16. An apparatus as in claim 13 wherein said transmitter transmits said signal and receives said reflected signal.

17. An apparatus as in claim 13 wherein a phase change of said signal detected at said first sensor is analyzed to detect multiple documents.

18. An apparatus as in claim 13 wherein an amplitude change of said signal detected at said first sensor is analyzed to detect multiple documents.

19. An apparatus as in claim 13 wherein a phase change of said signal detected at said first sensor or an amplitude change of said signal detected at said first sensor is analyzed to detect multiple documents.

20. An apparatus as in claim 13 wherein a phase change or an amplitude change of said signal detected at either of said first sensor or said second sensor indicates a presence of multiple documents.

21. A method for detection of multiple documents in a document transport system consisting of the steps:
   transmitting a signal through a document feed path;
   reflecting said signal through said document feed path;
   detecting said reflected signal at a first sensor;
   detecting said reflected signal at a second sensor;
   analyzing said reflected signal received by said first sensor to detect multiple documents; and
   analyzing said signal received by said second sensor to detect multiple documents.

22. The method of claim 21 wherein said signal is an ultrasonic signal.

23. A method as in claim 21 wherein said first sensor and said second sensor are separated by at least one-half a width of said feed path.

24. A method as in claim 21 wherein said transmitter is located at a center position with respect to a width of said document transport system.

25. A method as in claim 24 wherein said first sensor is located adjacent said transmitter on a first side of said transmitter; and said second sensor is located adjacent said transmitter on a first side of said transmitter and on a side opposite said first sensor.

26. A method as in claim 21 wherein said first sensor, said second sensor, and said transmitter are equally spaced across said feed path.

27. A method as in claim 21 wherein said transmitter transmits said signal and receives said reflected signal.

28. A method as in claim 21 wherein a phase change of said signal detected at said first sensor is analyzed to detect multiple documents.

29. A method as in claim 21 wherein an amplitude change of said signal detected at said first sensor is analyzed to detect multiple documents.

30. A method as in claim 21 wherein a phase change of said signal detected at said first sensor or an amplitude change of said signal detected at said first sensor is analyzed to detect multiple documents.

31. A method as in claim 21 wherein a phase change or an amplitude change of said signal detected at either of said first sensor or said second sensor indicates a presence of multiple documents.

* * * * *

UNITED STATES PATENT AND TRADEMARK OFFICE
CERTIFICATE OF CORRECTION

PATENT NO. : 6,913,259 B2
DATED : July 5, 2005
INVENTOR(S) : Daniel P. Phinney et al.

It is certified that error appears in the above-identified patent and that said Letters Patent is hereby corrected as shown below:

Column 4,
Line 54, after "as in claim" insert -- 1 --.

Signed and Sealed this

Thirtieth Day of August, 2005

JON W. DUDAS
*Director of the United States Patent and Trademark Office*